United States Patent
Knollmann et al.

(10) Patent No.: US 6,300,295 B1
(45) Date of Patent: Oct. 9, 2001

(54) DENTURE CLEANSING COMPOSITION

(75) Inventors: Rainer Knollmann, Herford; Monika Van de Loecht-Blasberg, Weinheim, both of (DE)

(73) Assignee: Kukident GmbH, Weinheim (DE)

( * ) Notice: Subject to any disclaimer, the term of this patent is extended or adjusted under 35 U.S.C. 154(b) by 0 days.

(21) Appl. No.: 09/367,681

(22) PCT Filed: Feb. 17, 1998

(86) PCT No.: PCT/EP98/00897

§ 371 Date: Nov. 18, 1999

§ 102(e) Date: Nov. 18, 1999

(87) PCT Pub. No.: WO98/35647

PCT Pub. Date: Aug. 20, 1998

(30) Foreign Application Priority Data

Feb. 17, 1997 (DE) .............................. 197 05 930

(51) Int. Cl.⁷ ...................................................... A61R 7/30
(52) U.S. Cl. .............................................................. 510/116
(58) Field of Search ............................................... 510/116

(56) References Cited

U.S. PATENT DOCUMENTS

| 4,155,868 | 5/1979 | Kaplan et al. . |
| 4,180,467 | 12/1979 | Barth . |

FOREIGN PATENT DOCUMENTS

| E 45 495 | 3/1990 | (AT) . |
| 21 33 710 B2 | 7/1977 | (DE) . |
| 38 12 693 C2 | 3/1990 | (DE) . |
| 39 34 390 C2 | 12/1993 | (DE) . |
| 00 10 412 A1 | 4/1980 | (EP) . |
| 02 58 186 A2 | 3/1988 | (EP) . |
| 0787481 | 8/1997 | (EP) . |
| 0787482 | 8/1997 | (EP) . |
| 15 27 010 | 10/1978 | (GB) . |
| WO 94 26 246 A1 | 11/1994 | (WO) . |
| WO A 9619193 | 6/1996 | (WO) . |
| WO A 973 5555 | 10/1997 | (WO) . |

*Primary Examiner*—Necholus Ogden
*Assistant Examiner*—John M Petruncio
(74) *Attorney, Agent, or Firm*—Knobbe, Martens, Olson & Bear, LLP

(57) ABSTRACT

A denture cleansing composition for dissolution in water to form a cleansing bath with a initial pH of not more than 4.5. The composition contains at least one bleaching agent, at least one tartar removal agent, and at least one carbonate or bicarbonate. A combination of citric acid and malic acid as tartar removal agents results in increased tartar removal compared to citric acid or malic acid alone. The bleaching agent is an alkali metal or alkaline earth persulfate, perborate, percarbonate, or perphosphate. Preferably, the active agents are present as visually discrete particles.

The composition is more stable than compositions having bisulfate as a tartar removal agent and avoids the unpleasant taste due to bisulfate. Potassium monopersulfate is an effective bleaching agent. Sodium bicarbonate and carbonate act as pH regulators and as effervescence agents to avoid gradient formation in the bath and to help remove particles from the dentures.

13 Claims, No Drawings

DENTURE CLEANSING COMPOSITION

This is the U.S. national phase under 35 U.S.C. § 371 of International Application PCT/EP98/00897, filed Feb. 17, 1998.

The present invention relates to a denture cleansing composition, preferably for dissolution in water to form a denture cleansing bath having an initial pH of about 4.5 or less and to a denture cleansing tablet made therefrom.

Various compositions are known in the art of the cleansing and care of dental prosthesis, such as dentures and braces, which compositions are typically dissolved in water in order to form a cleansing bath.

Known denture cleansing compositions may be one or two phase compositions.

Furthermore, denture cleansing compositions are known which are acidic for the cleansing step. Such compositions typically include sulphuric or hydrochloric acid and have disadvantages, many of which are inherent to the handling of the tablets during production, including packaging, and to the use by the final consumer which have a negative effect on their acceptability.

Alternatively, citric acid may be used in denture compositions to create an acidic environment for the cleansing procedure. However, the use of citric acid causes the denture cleansing tablets to have poor hardness properties. It is, however, important for the compositions to have good hardness properties to provide an efficient tablet production process.

Denture cleansing compositions are known which contain a bisulfate as the tartar removal agent. Such bisulfate based denture cleansing compositions have a poor temperature stability and cause an unfavourable "chemical" taste to the dentures, that have been treated with these compositions, that can be tasted by the customer. Such a composition is as described and exemplified in EP 010 412.

It is an object of the present invention to provide a denture cleansing composition which exhibits good tartar removal activity and good shelf life stability, while at the same time providing good hardness properties so that the denture cleansing tablet can be easily made therefrom.

The inventors have now found a composition, for use in dental cleansing, that reduces or overcomes the disadvantages of known denture cleansing compositions and particularly solves the above specified problems.

According to the present invention there is provided a denture cleansing composition (preferably for dissolution in water to form a cleansing bath having a pH of no more than 4.5) comprising i) one or more bleaching agents ii) at least one, preferably two, tartar removal agents; and iii) carbonates and/or bicarbonates characterised in that the tartar removal agent(s) is or are selected from citric acid and malic acid.

Preferably the compositions according to the invention are one phase compositions. Preferably the compositions are effervescent compositions.

Preferred bleaching agents are selected from alkali metal and alkaline earth metal or ammonium persulfates, perborates, percarbonates and perphosphates, especially selected from potassium and sodium persulfate. Such bleaching agents are described in WO97/35555, the contents of which are incorporated herein by reference.

Preferably the bleaching agent is present in an amount of 10 to 40% by weight, more preferably, 15 to 30%.

In this Specification all percentages are by weight unless indicated to the contrary.

Preferably in a composition according to the invention, the tartar removal agents are solely citric acid and malic acid. Preferably the amount of tartar removing agent is 10 to 50%, more preferably 20 to 40%.

Preferred carbonates are selected from alkali metal carbonates and/or bicarbonates, more preferably, sodium carbonate. Preferably the carbonates and/or bicarbonates are present in an amount of 5 to 30% more preferably 10 to 25 by weight.

Further according to the invention, there is provided a denture cleansing composition comprising:

i) 10 to 40% of one or more bleaching agents, ii) 10 to 50% of tartar removal agents selected from citric acid and/or malic acid; and iii) 5 to 30% of one or more carbonates and/or bicarbonates.

In a first embodiment of the present invention, the denture cleansing composition comprises i) one or more bleaching agents, ii) one or two tartar removal agents and iii) sodium carbonate.

In a preferred embodiment, the bleaching agent is a permonosulphate, more preferably an alkali metal or alkaline earth metal permonosulphate, most preferably, potassium or sodium monopersulphate.

The composition may also include at least one enzyme, preferably a lipase, a protease and/or a glycosidase.

Further according to the present invention, the composition may contain one or more further additives, such as flavouring agents, dyestuffs, malodour counteractants, agents for plaque removal, agents for surface modification, agents for natural teeth preservation, agents for saliva regulation, agents for bad breath neutralization, agents for freshness and anti-soil-/anti-bacterial agents or a mixture of two or more thereof.

The above-specified additives are preferably present in an amount of 0 to 10% by weight. These additives, are suitable for both supporting the cleansing mechanism and conferring an aesthetic appealing appearance to the cleansing bath. Furthermore, they support in a general manner the hygiene of the oral cavity of the denture wearing person, including any remaining natural teeth. Such additives are known to the one skilled in the art.

In a further embodiment of a composition of the invention, at least one of the components selected from the tartar removal agents, carbonates, bicarbonates, enzymes and further additives, are present as visually discrete particles.

In a particularly preferred embodiment of a composition of the invention, the tartar removal agents and additives, i.e. flavouring agents and malodour counteractants, dyestuffs, agents for plaque removal, agents for surface modification, agents for natural teeth preservation, agents for saliva regulation, agents for bad breath neutralization, agents for freshness and anti-soil-/anti-bacterial agents or a mixture of two or more thereof, citric acid and/or malic acid is (are) present as visually discrete particles.

The term "denture" also includes prosthesis including partial prosthesis, any tooth substitute materials and braces as well as any elements thereof.

The inventors have surprisingly discovered that tartar is very efficiently dissolved and thus removed by denture cleansing compositions according to the present invention. Furthermore, they have found that the composition itself is significantly more stable than the compositions of the prior art, which means that they have a good shelf life. Also the pressing of the denture cleansing compositions into tablets is easier and allows the formation of tablets of improved hardness and improved shelf life.

The preferred combination of citric acid and malic acid as tartar removal component in a denture cleansing composition results in increased tartar removal compared to the use of citric or malic acid alone.

As compared to the compositions that have bisulfate as the tartar removal agent known in the art, the compositions of the invention are more stable and avoids the unpleasant taste arising from the bisulfate.

The inventors believe that the excellent pressing characteristics of the denture cleansing composition of the invention is based on the preferred presence of both citric and malic acids. Malic acid seems to be particularly suitable for conferring improved hardness to tablets of the compositions of the invention. However, the presence of malic acid causes an increased stickness of the tablets formed therefrom which is undesirable where a fast production process is required.

Under these circumstances, the inventors have surprisingly discovered that by combining malic acid with citric acid, the citric acid functions as an anti-adhesive, thus allowing production of denture cleansing tablets with increased hardness and good pressing and thus production characteristics.

A further advantage of the denture cleansing compositions of the invention is a good effervescence which results in avoidance of gradient formation in the cleansing bath and also has a mechanical cleansing effect.

Advantageously, the denture cleansing compositions of the invention, and particularly denture cleansing tablets produced therefrom, allows for faster dissolution which as such can be controlled with certain limits as known by one skilled in the art. This aspect is particularly important for the final consumer as typically a time period of two to ten minutes is desired for the denture cleansing process and the denture cleansing compositions of the invention allow dissolution times to be closer to the lower limit of the above identified time period.

The enzymes which can optionally be added to the denture cleansing compositions of the invention may contribute to cleansing and support the other cleansing mechanism, respectively.

Further advantages arise from the fact that the bleaching agent, the tartar removal agents, the above-specified additives and the carbonate/bicarbonate of the denture cleansing composition may, individually or in combination, be present as visually discrete particles. It is possible that within the above-specified components, each of the compounds forming said components may be present as said particles, either alone or in combination.

Accordingly, it is possible that citric acid and/or malic acid is/are present as visually coloured particles in a composition according to the invention.

This is advantageous with regard to the manufacturing process as the manufacturing process can easily be controlled by visual detection of the individual particles. Such particles are also suitable to increase mechanical stability, particularly of tablets produced from a denture cleansing composition according to the present invention. Finally, such particles allow an efficient and controllable release kinetic of the compounds forming them.

Beyond those components specified above the compositions of the invention may comprise further components and compounds, as is obvious for one skilled in the art, such as, for example, ionic surfactants, binding agents and bursting agents and the like. These are preferably present in an amount of 0 to 15% by weight.

The acidic components must be sufficient to create preferably an initial pH of about 4.5 or less in the cleansing bath.

The optionally added enzymes might be in the case of proteases, pepsin, papain, acidic and alkaline proteases, in the case of glycosidases, glucanases such as endoglucanases and exoglucanases, and most preferably amylases. In principle, the enzymes might be of animal, plant or microbiological origin or they may be produced by means of gene technology. The enzymes may be used, individually or in combination, in a purified form or associated with other proteinaceous material.

While not wishing to be bound by theory, the inventors believe that the above-specified advantages, relating to improved cleansing efficiency of the denture cleansing compositions of the invention is based on the ability of the tartar removal agent, i.e. citric acid and/or malic acid to dissolve or complex calcium, magnesium or other metal ions. Because of this, tartar and persistent plaque are removed as well as stubborn stains, especially those included in the tartar. The active oxygen released by the bleaching agent removes organic material present as film or plaque on the denture by oxidation. Furthermore, the oxygen acts, similarly to the acids, in bactericidal and smell reduction. It is noteworthy that there is no adverse effect on the denture forming material, including metal parts optionally contained therein, as a result of use of denture cleansing compositions of the invention.

The invention will now be illustrated by the following examples.

EXAMPLES 1 TO 10

Table 1 shows examples of the denture cleansing composition according to the present invention.

The following function can be attributed to the individual compounds as listed in said table.

Citric acid and malic acid dissolve carbonate salts of the tartar and in addition by complexing calcium and magnesium ions, remove the tartar. They function as complexing agents and are part of the effervescence system when the composition is dissolved in water.

Potassium monopersulfate is the oxygen active bleaching agent.

Sodium bicarbonate and sodium carbonate act as pH regulators and effervescence agents. Under the influence of the acids, gaseous carbon dioxide is released from the (bi)carbonate which supports the cleansing process by its mechanical impact and, for example, removes food remainders.

Sulfamic acid serves as chlorine acceptor and particularly avoids the unpleasant chlorine smell and taste.

Sodium dodecyl benzene sulphonate is a surfactant, emulsifier and foaming agent which reduces the surface tension of water so that the cleansing bath may reach areas of the denture otherwise hardly reachable and may be effective there.

Sodium sulfate serves as filler and particularly as tabletting aid in the manufacture of the denture cleansing tablet from the inventive denture cleansing composition. PEG-75 and PG-150 are tabletting agents.

"Flavour" describes a flavouring agent and C.I. 19140 and C.I. 42090 are green dyes which confer a green colour to an aliquot of water upon dissolution of the denture cleansing composition.

Example 1 shows the inventive denture cleansing composition which comprises a citric acid as tartar removal component.

Example 2 is a further embodiment of the inventive denture cleansing composition which comprises in addition to citric acid also malic acid.

Examples 3 to 6 are further embodiments of the composition illustrated in example 1, wherein the content of an enzyme or a combination of several enzymes is realized. Beyond the combination of three enzymes as shown in examples 3 to 6 it is, of course, also possible to realize a combination of a protease with an amylase and, more generally, glycosidases, respectively, of protease with lipase and of amylase, and more generally glycosidases, with lipases.

Examples 7 to 10 are further embodiments of the denture cleansing composition according to example 2 and the above-given explanations related to combining various enzymes therein apply here, too.

The enzymes according to the above-given examples are commercially available preparations and, more particularly, Novozym® 243 was used as protease, Termamyl® as amylase and Lypozym® as lipase.

The above specified amounts are expressed as % by weight.

samples which have been dipped into hot water, looking for microscopic changes such as colour changes or metal corrosion. The rating was performed using three categories, namely "minor", "middling" and "pronounced". The microscopic examination was performed by independent visual examination of two persons after 35, 70, 105, 140, 175, 210, 245, 280, 315, 350, 385 and 400 test cycles.

The study revealed that even after 400 treatments with the denture cleansing composition according to the present which exhibits an excellent tartar removal efficiency, none of the tested samples had experienced visible changes.

The following is an example for a denture cleansing composition according to the invention—Example 2.

Summary of in-vitro- and in-vivo-test results

Background

Example 2 is a special cleaner which removes stubborn Strains and Tartar.

For the evidence of this efficacy, a number of in-vitro- and in vivo-analysis were carried out during the product development, which confirm the removal of stubborn stains and tartar and which are described summarized in the following.

TABLE 1

| Compound | Ex. 1 | Ex. 2 | Ex. 3 | Ex. 4 | Ex. 5 | Ex. 6 | Ex. 7 | Ex. 8 | Ex. 9 | Ex. 10 |
|---|---|---|---|---|---|---|---|---|---|---|
| Potassium monopersulfate | 24,00 | 20,00 | 24,00 | 24,00 | 24,00 | 24,00 | 20,00 | 20,00 | 20,00 | 20,00 |
| Sodium bicarbonate | 2,50 | 7,50 | 2,50 | 2,50 | 2,50 | 2,50 | 7,50 | 7,50 | 7,50 | 7,50 |
| Sodium carbonate | 2,50 | 5,00 | 2,50 | 2,50 | 2,50 | 2,50 | 5,00 | 5,00 | 5,00 | 5,00 |
| Anhydrous Citric acid | 36,00 | 25,00 | 36,00 | 36,00 | 36,00 | 36,00 | 25,00 | 25,00 | 25,00 | 25,00 |
| Malic acid | — | 10,00 | — | — | — | — | 10,00 | 10,00 | 10,00 | 10,00 |
| Sodium polyphosphate | 4,00 | — | 4,00 | 4,00 | 4,00 | 4,00 | — | — | — | — |
| Sodium hexameta phosphate | 8,30 | — | 8,30 | 8,30 | 8,30 | 8,30 | — | — | — | — |
| Sulfamic acid | 3,00 | 4,00 | 3,00 | 3,00 | 3,00 | 3,00 | 4,00 | 4,00 | 4,00 | 4,00 |
| Anhydrous Sodium sulfate | 12,40 | 21,20 | 10,90 | 10,90 | 10,90 | 7,90 | 19,70 | 19,70 | 19,70 | 19,70 |
| Sodium dodecyl benzene sulfonate | 0,30 | 0,30 | 0,30 | 0,30 | 0,30 | 0,30 | 0,30 | 0,30 | 0,30 | 0,30 |
| Flavour | 1,00 | 1,00 | 1,00 | 1,00 | 1,00 | 1,00 | 1,00 | 1,00 | 1,00 | 1,00 |
| PEG 4000 | 0,70 | 0,70 | 0,70 | 0,70 | 0,70 | 0,70 | 0,70 | 0,70 | 0,70 | 0,70 |
| Dye C.I. 19140/42090 | 0,0015 | 0,0015 | 0,0015 | 0,0015 | 0,0015 | 0,0015 | 0,0015 | 0,0015 | 0,0015 | 0,0015 |
| Protease | — | — | 1,50 | — | — | 1,50 | 1,50 | — | — | 1,50 |
| Amylase | — | — | — | 1,50 | — | 1,50 | — | 1,50 | — | 1,50 |
| Lipase | — | — | — | — | 1,50 | 1,50 | — | — | 1,50 | 1,50 |
| Total | 100,00 | 100,00 | 100,00 | 100,00 | 100,00 | 100,00 | 100,00 | 100,00 | 100,00 | 100,00 |

Upon dissolution of the denture cleansing compositions of table 1 a pH of about 3 was observed. Studies have been carried out in which the tartar removal activity of the compositions of the invention have been tested on natural tartar as well as model substances. Also tests have been performed aiming at compatibility of the composition with the denture material. In these studies, chromium/cobalt or gold alloys and also polymers, such as auto-polymerized polymethylmethacrylate, have been used. Tablets prepared from the inventive denture cleansing compositions were added to 150 ml tap water at an initial temperature of 50° C. and the denture materials dipped therein for ten minutes. After that the material samples have been rinsed twice with cold water and the procedure has been repeated 400 times. The material samples were compared to material samples which have been stored in a dry condition and to material Tartar means hard, dark coloured sedimentations on and between the teeth, which are built up by mineralization of plaque. By inclusion of different food-residues these sedimentations can take on also other colourations (=stubborn discolourations). In the case of natural teeth tartar can be removed only mechanically (in mouth). Just as with the natural teeth tartar is being built up also on dental prothesis. This one can also be removed mechanically. As dentures are mostly cleaned outside the mouth, a special cleaner represents a suitable method for the removal of tartar. Especially pH-acidic cleaners are suitable because of the mineral-composition of the tartar.

The essential part of the crystals of the supra- and subgingivale tartar are calciumphosphates like tetra-calciumhydrogen-phosphate, calciumhydrogenphosphate (Brushit), tricalciumphosphate (Whitlockit), calciumhydroxylapatit and calciumcarbonates.

Calciumcarbonate (=lime) but also calciumphosphates are especially well dissolved in pH-acidic cleaning-solutions than in pH-neutral ones.

1) pH-value/fruit-acid efficacy of Example 2

Example 2 has a high concentration of fruit-acids (in total 35% citric acid and malic acid). In addition, as the contents of alkaline, neutralizing ingredients are lower, Example 2 shows an acidic pH-value of approx. 3 in the cleaning solution. The pH-values of the cleaning solutions of conventional denture cleaner products are in the pH-neutral range of 6–8.

Fruit-acids and the acidic pH-value show special efficacies.

Calciumcarbonate, a mineral-ingredient of tartar is significantly better dissolved by Example 2 compared with pH-neutral cleaner tablets:

| Example 2: | 10, 6 mg |
|---|---|
| Steradent-Original: | 5, 9 mg |
| Cleaner I pH 6–8: | 1, 1 mg |

2) Efficacy of Example 2 against tartar/stubborn discolourations

With the following tests this efficacy is being proved:

a) "CaHPO$_4$/Calciumhydrogenphosphate-Dissolution Ability"

Calciumhydrogenphosphate, a mineral-ingredient of the normal tartar, is dissolved significantly better by Example 2 than by conventional cleaning tablets:

| Example 2: | 95, 4% |
|---|---|
| Cleaner I pH 6–8: | 75, 4% |
| Cleaner III pH-alkaline: | 59, 0% | b) "Ca$_3$(PO$_4$)$_2$/Tricalciumphosphate Dissolution Ability"

Tricalciumphosphate, also a main ingredient of the natural tartar, is dissolved significantly better by Example 2 than by conventional cleaning tablets:

| Example 2: | 56, 0% |
|---|---|
| Cleaner I with pH 6–8: | 2, 1% |
| Steradent-Original: | 3, 2% | c) "Tartar Dissolution Ability (quantitative)"

In this comparative test natural tartar was used, that was collected by dentists. The efficacy of the cleaners was determined analytically via the calcium- and phosphorus-contents. This semi-in-vivo test shows also the superior and significantly higher efficacy of Example 2 in the case of dissolution of natural tartar:

|  | via Calcium-determ. | via Phosphorus-determ. |
|---|---|---|
| Example 2: | 58% | 67% |
| Cleaner I with pH 6–8: | 12% | 12% |
| Cleaner II with pH 6–8: | 6% | 7% | d) "Tartar Dissolution Ability (qualitative)"

In this test dentures that are no longer in use (received from dental laboratories) but that have been used for long term and showed strong tartar deposits, were cleaned in a standardized procedure with Example 2. As a result a reduction of tartar is identifiable after 3 usages and after 66 tablet cleanings (1 consumer packaging) a practically complete cleaning is given. The efficacies were documented by photos.

The tests a), b) and c) as well as "Calciumcarbonate-Dissolution" show comparative tests of different denture cleaning tablets, the test d) with realistic dentures was just carried out with Example 2. Example 2 is significantly better than the prior art.

The features disclosed in the foregoing description and/or in the claims may, both separately and in combination thereof, be material for realising the invention in diverse forms thereof.

What is claimed is:

1. A denture cleansing composition for dissolution in water to a cleansing bath having a pH of not more than 4.5, comprising:

i) at least one bleaching agent;

ii) a tartar removal agent of both citric acid and malic acid; and iii) at least one compound selected from the group consisting of carbonates and bicarbonates.

2. A composition according to claim 1, wherein the tartar removal agent is up to 50% by weight of the composition.

3. A composition according to claim 1, wherein the at least one bleaching agent comprises at least one alkali metal or alkaline earth metal persulfate, perborate, percarbonate, or perphosphate.

4. A composition according to claim 1, wherein the composition further comprises at least one enzyme.

5. A composition according to claim 4, wherein at least one of the materials selected from the group consisting of plaque removal agents, carbonates, bicarbonates, enzyme and any further additives is present as visually discrete particles.

6. A denture cleansing tablet comprising a composition according to claim 1 and a tabletting material.

7. A denture cleansing tablet according to claim 6, wherein the tablet comprises:

i) 90 to 97% of a composition according to claim 1; and ii) 3 to 10% of a tabletting material.

8. A denture cleansing composition according to claim 1, wherein the composition comprises:

i) 10 to 40% of said at least one bleaching agent;

ii) 10 to 50% of said tartar removal agent of both citric acid and malic acids; and iii) 5 to 30% of said at least one compound selected from the group consisting of carbonates and bicarbonates.

9. A denture cleansing composition which, upon dissolution in water results in a cleansing bath with pH of not more than 4.5, comprising:

i) at least one bleaching agent;

ii) citric acid and malic acid; and iii) at least one compound selected from the group consisting of carbonates and bicarbonates.

10. A method for cleansing dentures comprising dissolving a composition according to claim 1 in water and adding the dentures to be cleansed.

11. A composition according to claim 4, wherein said at least one enzyme is selected from the group consisting of proteases, lipases, and glycosidases.

12. A composition according to claim 9, further comprising at least one additive.

13. A method according to claim 10, wherein said adding is before, after, or at the same time as said dissolving.

* * * * *